United States Patent [19]

Penzo et al.

[11] Patent Number: 4,973,766
[45] Date of Patent: Nov. 27, 1990

[54] PROCESS FOR RECOVERING PHENOL FROM A RECTIFICATION PURGE

[75] Inventors: Renzo Penzo; Paolo Reggiani; Claudio Spaggiari, all of Mantova, Italy

[73] Assignee: Montedipe S.r.l., Italy

[21] Appl. No.: 425,106

[22] Filed: Oct. 23, 1989

[30] Foreign Application Priority Data

Dec. 2, 1988 [IT] Italy ................................ 22823 A/88

[51] Int. Cl.$^5$ ...................... C07C 37/70; C07C 37/82
[52] U.S. Cl. .................................. 568/754; 568/749; 568/798
[58] Field of Search ........................ 568/749, 754, 798

[56] References Cited

U.S. PATENT DOCUMENTS 4,262,150 4/1981 Pujado ............................... 568/754
4,262,151 4/1981 Pujado ............................... 568/754

Primary Examiner—Werren B. Lone
Attorney, Agent, or Firm—Morgan & Finnegan

[57] ABSTRACT

A process for recovering phenol from a rectification purge containing various organic foreign matters, which includes the steps of subjecting the purge to an extraction operation, using, as an extracting solvent, an aqueous solution of an alkali metal phenate.

18 Claims, 3 Drawing Sheets

PROCESS FOR RECOVERING PHENOL FROM A RECTIFICATION PURGE

BACKGROUND OF THE INVENTION

1. Field of the Invention

When phenol is manufactured by cleavage of cumene hydroperoxide, a rough phenol is obtained, which has to be rectified by hydrodistillation or by extractive distillation. In either process, two distillation columns are used. In the upstream (or first) column, at the top, are separated foreign matters, mostly a light cut, consisting of mesityl oxide, hydroxyacetone, cumene, alpha-methylstyrene, 2-methyl-benzofuran and other organic substances, which are present (as impurities) in the pure phenol; and in the downstream (or second) column, the pure phenol is distilled. The purge obtained from the top of the first column contains phenol, in a concentration from 20% to 90% by weight, usually from 50% to 80% by weight. The phenol contained in the purge of the first column can be recovered, as is known, by salification with a strong base, for instance, caustic soda; with the resulting sodium phenate, remaining dissolved in the aqueous phase, subsequently acidified with an acid such as $H_2SO_4$, $H_2CO_3$ or other similar acids, thereby containing free phenol. To obtain a complete (or substantially complete) shifting of phenol to the aqueous phase, in the form of a salt, it is necessary to operate with an excess of base and, when NaOH is used as a base, the excess usually amounts to a quantity ranging from 1% to 30% of the maximum amount convertible to sodium phenate. Therefore, consumption of base is a considerable burden of the known process.

2. Discussion of the Prior Art

European patent No. 28522 suggests, as an alternative process, the recovery of phenol from the purge of the first column by means of steam distillation. However, in this suggested process the costs connected with the use of steam are quite dear and are not neglectable.

As a matter of principle, it would be possible to recover phenol by means of an extraction with $H_2O$ this expedient would allow the avoidance of the use of NaOH or steam and the resultant disadvantages associated with each. However, the distribution coefficient of phenol between the aqueous and organic phases in the purge of the first column would require the feeding of a considerable water amount to the plant, which would result in an increase of the power (and reactants) consumption. In this case, the cost, on the whole, would be even higher than the cost arising from the recovery by means of salification with NaOH.

The applicants have now found a method which permits the recovery of phenol from the rectification purge in a very simple manner and with yields similar to those obtainable by use of salification with NaOH or from the steam distillation processes described above, while avoiding any consumption of NaOH or of steam.

SUMMARY OF THE INVENTION

In its broadest aspect, the invention concerns a process for recovering phenol from a rectification purge, containing from 20 to 90% by weight of phenol, in addition to various foreign matters or impurities, in particular, mesityl oxide, hydroxyacetone, alpha-methylstyrene and 2-methylbenzofuran. The process includes the steps of subjecting the purge of a rectification step to an extraction operation, using, as an extracting solvent, an aqueous solution of an alkali metal phenate, for instance sodium phenate ($C_6H_5ONa$).

DETAILED DESCRIPTION OF THE INVENTION

In a plant for the synthesis of phenol, by cleavage of cumene hydroperoxide, various aqueous solutions of sodium phenate are available. The total amount of aqueous solution of sodium phenate is by far greater than the purged mass to be treated. The applicants have surprisingly found that the extraction of said sodium phenate solution can be as effective as the conventional extraction with soda, wherefore it is possible to carry out said phenol recovery practically cost-free. In other words, the advantage of the invention resides in the presence of an alkali metal phenate which causes an unexpected increase in the distribution coefficient of phenol between the aqueous and organic phases, thereby promoting the phenol solubilization in the inorganic phase.

The aqueous solution of sodium phenate, which is utilized in this process may contain, in addition to the phenate, small amounts of free NaOH. In such a case, a small salification of phenol will take place, which, of course, does not diminish the usefulness of the invention.

The invention can be carried out in various ways. The extraction process, for instance, can be performed in a particularly advantageous way when:

the aqueous solvent contains from 1 to 15% and preferably from 5 to 15% by weight of sodium phenate;

the extraction temperature ranges from room temperature to 90° C. and preferably from 40° C. to 80° C.;

the extracting solvent amount ranges from 1 to 15 and preferably from 5 to 15 parts by weight per each part of purge;

the extraction is performed continuously, the reactants being fed (in counter-concurrent) into an apparatus consisting of at least two mixers and of at least two decanters, or into an apparatus, which allows one to perform a plurality of extraction steps, without any need to separate the two flows, preferably taking care to assure that the organic phase be the continuous phase and that the aqueous phase be the dispersed phase;

said apparatus can advantageously have a tubular shape and can be filled with packing bodies, preferably of stainless steel or of another material preferably wetted by the organic phase; most preferably when said packing bodies are RASCHIG rings or PALL rings.

The following examples are merely for illustrative purposes and do not limit the scope of the invention.

EXAMPLE 1

Part "A" (extractive distillation)

Figure 1:
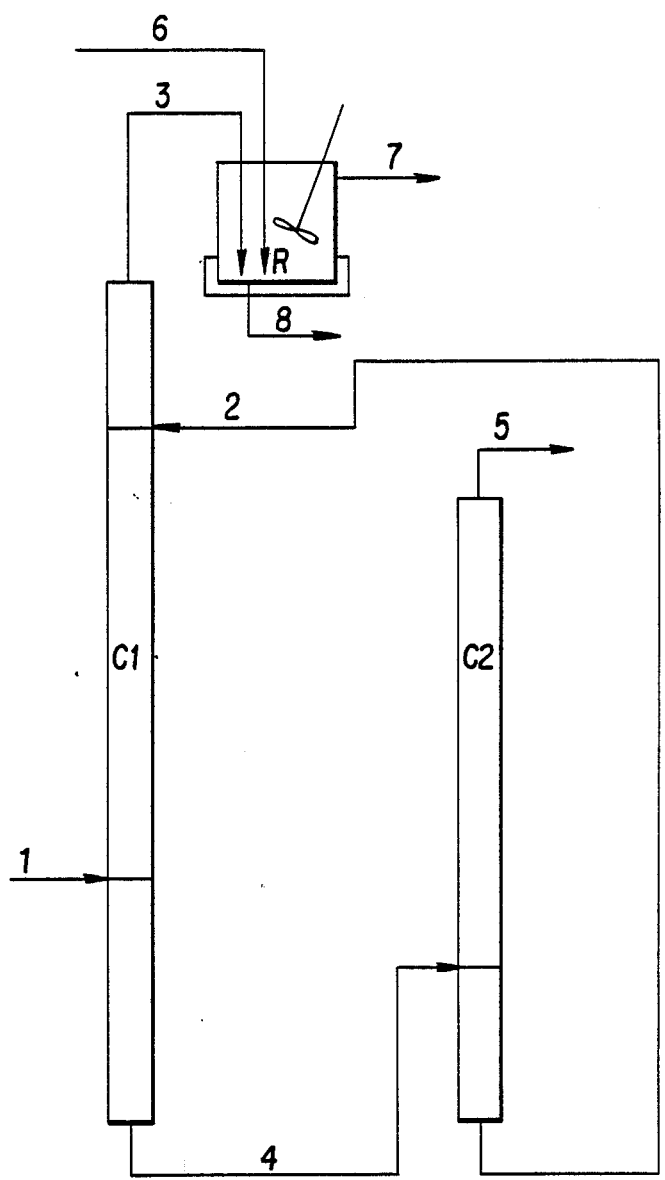
FIG. 1 is a schematic representation of a two-column system for the recovery of phenol obtained from the cleavage of cumene hydroperoxide.

Referring to FIG. 1, rough phenol (1), having a titre of about 95% (by weight) and coming from the cleavage of cumene hydroperoxide (already separated from acetone, from most of the cumene and from the high-boiling impurities) is fed to extraction column (C1), which is also fed with a mixture of diethylene glycol (DEG) and phenol (2), coming from the bottom of column (C2). The separation of almost all the impurities (3) (in particular alpha-methylstyrene and other hydrocarbons, hydroxyacetone, mesityl oxide, 2-methylbenzofuran and so on) occurs at the top of column (C1), whereas a mixture (4) of phenol and DEG, which is fed to column (C2), was obtained from the bottom of said column (C1). From the top of column (C2), pure phenol (5) was obtained, whereas from the bottom of column (C2) a phenol/DEG mixture was obtained, which was recycled to column (C1). The refluxes (not indicated in the figure) of both columns were realized with their respective head condensates.

Part "B" (recovery of phenol from the purge)

100g of head product (3) of column (C1), containing 60% by weight of phenol, 1% by weight of water and 39% by weight of organic impurities, were fed to an extractor (R) having a volume of about 1,000 cm$^3$, equipped with a heating jacket, baffles and a rotary stirrer (500 r.p.m.). Said impurities consisted (for the most part) of mesityl oxide, hydroxyacetone, alpha-methylstyrene and 2-methyl-benzofuran. 500 g of an aqueous solution (6), containing 15% by weight of sodium phenate, flowing from another area of the phenol synthesis plant, were conveyed to the same apparatus. The temperature was raised to 50° C., stirring was carried on for 15 minutes and the whole was then allowed to rest (still at 50° C.) for a further 60 minutes. An organic (upper) phase (7) and an aqueous (lower) phase (8) were obtained; the results, reported in Table 1, reveal a remarkable phenol shift towards the aqueous phase.

EXAMPLE 2

Example 1 was repeated using, as an extractant, an aqueous solution containing 10% by weight of sodium phenate; data and results are recorded in Table 1.

EXAMPLE 3

Example 1 was repeated using, as an extractant, an aqueous solution containing 5% by weight of sodium phenate; data and results are recorded in Table 1.

EXAMPLE 4 (COMPARATIVE)

Example 1 was repeated, replacing the addition of sodium phenate by the introduction of 500 g of pure (deionized) water. As shown in Table 1, the phenol shift to the aqueous phase is much lower when compared with the values obtained when sodium phenate is added.

EXAMPLES 5-6

Example 3 was repeated, varying the extraction temperature (70° C. and 90° C. respectively); the results are recorded in Table 2; they show that even a slight raising of the temperature leads to a considerable increase in the extraction yield.

EXAMPLE 7

Figure 2:
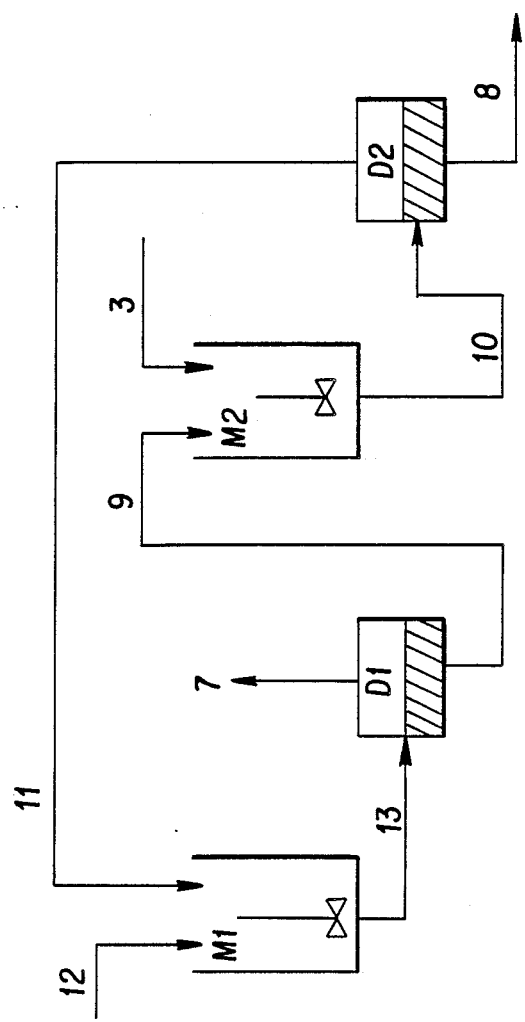
FIG. 2 is a schematic representation of an extraction system including two mixers and two decanters.

Example 3 was repeated carrying out the extraction by means of the apparatus system illustrated in FIG. 2. This system comprises two mixers (M1 and M2) and two decanters (D1 and D2). According to FIG. 2, 100 g/h of the head product (3) of column (C1), having the composition described in Example 1, was continuously fed to mixer (M2) along with the aqueous phase (9), separated in decanter (D1). The effluent from (M2) (10) was conveyed to decanter (D2), where the aqueous flow (8), containing all the extracted phenol, and the organic flow (11) were separated, the latter being fed to mixer (M1) along with 500 g/h of aqueous solution (12), at 5% by weight of sodium phenate. The liquid (13), flowing out from (M1) was transferred to separator (D1), where the aqueous flow (9), which was transferred to mixer (M2), and the organic flow (7) were separated. Data and results are recorded in Table 2, from which it is clear that, at the end of the extraction, only 9.7 g of phenol remained dissolved in 39.5 g of organic phase, which means that 83.8% of the starting phenol had been recovered in the aqueous phase.

EXAMPLE 8

A tubular extraction apparatus, equipped with a heating jacket, having an inner diameter of 75 mm and a height of 9 m (divided into three sections of 3 m each), was loaded with ceramic BERL saddles; size: ⅜" (9.5 mm). To the extractor bottom there was continuously fed 5 l/h of the rectification purge of Example 3, in countercurrent with 50 l/h (ratio=10:1) of an extracting aqueous solution containing 5% by weight of sodium phenate; the temperature was kept at 50° C. by means of warm water circulation. The aqueous flow formed the continuous phase while the organic flow formed the dispersed phase. Data and results are recorded in Table 3 from which it is clear that only 5.1% by weight of phenol was still in the organic phase at the end of the extraction, and that 96.4% of the starting phenol had been recovered in the aqueous phase.

EXAMPLE 9

Example 8 was repeated, replacing the ceramic saddles by stainless steel (AISI 316) RASCHIG rings; size: ⅜" (9.5 mm). The organic phase formed the continuous phase whereas the aqueous phase, contrary to Example 8, formed the dispersed phase. Data and results are recorded in Table 3, from which it is clear that only 0.20% by weight of phenol remained at the end of the extraction in the organic phase, and that 99.9% of the starting phenol had been recovered in the aqueous phase. Said residual phenol percentage in the impurities (0.20%) was lower than the phenol amount 0.30%), which remained after a conventional treatment was carried out, according to usual techniques, in a reactor equipped with a rotary stirrer, with a solution at 30% by weight of NaOH in such amount as to have, after salification, a residual NaOH amount equal to 0.6% by weight of the aqueous phase. Surprisingly, the excellent results of the present invention were obtained without the least consumption of caustic soda.

EXAMPLE 10

Part "A" (hydrodistillation)

Figure 3:
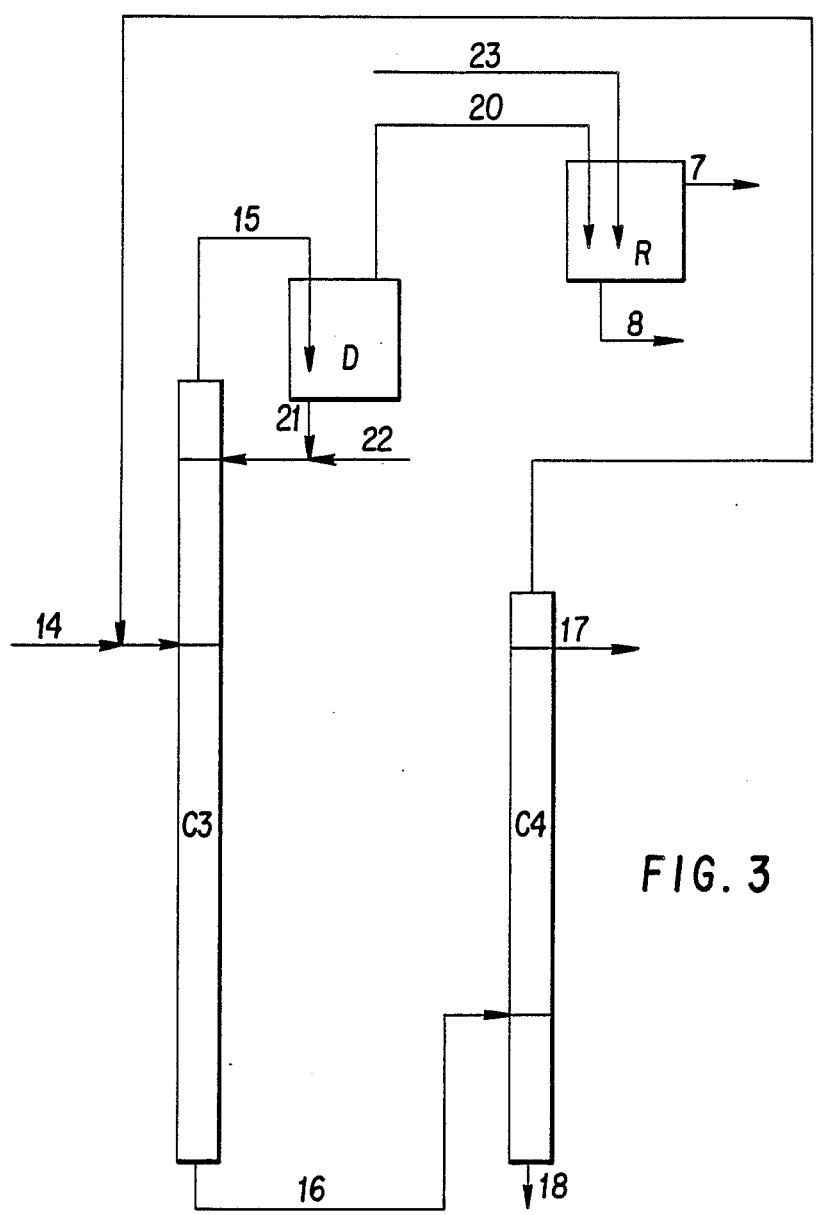
FIG. 3 is a schematic representation of a recovery system including a reflux tank.

According to FIG. 3, rough phenol (14) was fed to column (C3). The separation of the foreign matter (15) practically occurred at the top of column (C3), whereas, from the bottom of the column, a phenol stream (16) was obtained, which contained a very small amount of high-boiling foreign matter (and of H$_2$O). The phenol stream (16) was fed to a second column (C4). From second column (C4) a side cut of pure phenol (17) was obtained, whereas from its bottom a mixture of phenol and high-boiling products (18) was obtained, which was recycled to the process operations occurring upstream of column (C3). From the top of column (C4), a small purge of phenol and water (19) was obtained, which was again fed to column (C3). The head products (15) of the first column (C3) were made to flow to reflux tank D, where the impurities left, as organic phase (20), tank D, while the aqueous phase (21) was recycled as a reflux to the top of said column (C3), along with fresh make-up water (22), balancing the loss in the organic phase (20). The organic phase (2) then came into contact with a sodium phenate solution (23), as it is described in detail in part "B".

Part "B" (phenol recovery from the purge)

100 g of organic phase (20), coming from separator (D) and containing 60% by weight of phenol, 10% by weight of water and 30% by weight of organic foreign matter, was fed to an extraction apparatus like apparatus (R) of Example 1. Said foreign matter consisted, for the most part, of mesityl oxide, hydroxyacetone, alpha-methylstyrene and 2-methyl-benzofuran. By processing the organic phase as in Example 1, the results recorded in Table 4 were obtained, which reveal a remarkable shift of phenol from the organic towards the aqueous phase.

EXAMPLE 11

Example 10 was repeated using, as an extractant, an aqueous solution containing 10% by weight of sodium phenate; data and results are recorded in Table 4.

EXAMPLE 12

Example 10 was repeated using, as an extractant, an aqueous solution containing 5% by weight of sodium phenate; data and results are recorded in Table 4.

EXAMPLES 13 AND 14

Example 12 was repeated, varying the extraction temperature (70° C. and 90° C., respectively); the results are recorded in Table 5.

EXAMPLE 15

Example 12 was repeated, carrying out the extraction by means of the apparatus illustrated in FIG. 2, including two mixers (M1 and M2) and two decanters (D1 and D2), as is described in Example 7. Data and results are recorded in Table 5, from which it is clear that, at the end of the extraction, only 0.8 g of phenol remained in 31 g of the organic phase, which means that 98.7% of the starting phenol had been recovered in the aqueous phase.

EXAMPLE 16

To the bottom of the tubular extractor of Example 8, 5 liters/h of the hydrodistillation purge of example 12 were continuously fed (in countercurrent) with 25 1/h (ratio by volume=5:1) of an extracting aqueous solution containing 5% by weight of sodium phenate; the temperature was kept at 50° C. by hot water circulation. The aqueous phase was the continuous phase and the organic phase was the dispersed phase. Data and results are recorded in Table 6, from which it is clear that in the organic phase, at the end of the extraction, only 0.32% by weight of phenol remained, and that 99.8% of the starting phenol had been recovered in the aqueous phase.

EXAMPLE 17

Example 16 was repeated, replacing the BERL saddles by stainless steel (AISI 316) RASCHIG rings (⅜"). The organic phase was the continuous phase, whereas the aqueous phase, contrary to Example 16, was the dispersed phase. Data and results are indicated in Table 6, from which it is clear that in the organic phase, at the end of the reaction, less than 0.05% by weight of phenol remained and that more than 99.97% of the starting phenol had been recovered in the aqueous phase. The residual phenol (below 0.05% in the foreign matter) was by far lower than the amount of phenol (0.25%) which remains after a treatment carried out, according to conventional techniques, in an extractor equipped with a rotary stirrer, using a solution at 30% by weight of NaOH, in such amount as to have, after salification, a NaOH excess equal to 0.6% by weight of the aqueous phase. These excellent results were surprisingly obtained without any consumption of caustic soda.

EXAMPLES 18 AND 19

Examples 9 and 17 were repeated, replacing the RASCHIG rings by PALL rings; analogous results were obtained.

TABLE 1

| EXAMPLE | (% by weight) | | | |
|---|---|---|---|---|
| | 1 | 2 | 3 | 4 (*) |
| DATA | | | | |
| Temperature (°C.) | 50 | See Ex. 1 | See Ex. 1 | See Ex. 1 |
| RECTIFICATION PURGE | | | | |
| Amount (g) | 100 | See Ex. 1 | See Ex. 1 | See Ex. 1 |
| Phenol (%) | 60 | See Ex. 1 | See Ex. 1 | See Ex. 1 |
| $H_2O$ (%) | 1 | See Ex. 1 | See Ex. 1 | See Ex. 1 |
| Others (%) | 39 | See Ex. 1 | See Ex. 1 | See Ex. 1 |
| EXTRACTING SOLUTION | | | | |
| Amount (g) | 500 | See Ex. 1 | See Ex. 1 | See Ex. 1 |
| Sodium phenate (%) | 15 | 10 | 5 | 0 |
| RESULTS | | | | |
| ORGANIC PHASE: | | | | |
| Amount (g) | 44.0 | 48.0 | 55.0 | 61.2 |
| Phenol (%) | 29.6 | 35.6 | 41.8 | 47.7 |
| $H_2O$ (%) | 3.0 | 3.5 | 3.5 | 5.0 |
| Others (%) | 67.4 | 60.9 | 53.7 | 47.3 |
| INORGANIC PHASE: | | | | |
| Amount (g) | 556.0 | 551.1 | 545.0 | 538.8 |
| Sodium phenate (%) | 13.5 | 9.2 | 4.6 | — |
| Free phenol (%) | 8.45 | 7.7 | 6.8 | 5.7 |

TABLE 1-continued

| | (% by weight) | | | |
|---|---|---|---|---|
| EXAMPLE | 1 | 2 | 3 | 4 (*) |
| EXTRACTION YIELD (%) | 78.3 | 70.7 | 61.8 | 51.2 |

(*) Comparative

TABLE 2

| | (% by weight) | | |
|---|---|---|---|
| EXAMPLE | 5 | 6 | 7 |
| DATA | | | |
| Temperature (°C.) | 70 | 90 | 50 |
| RECTIFICATION PURGE | | | |
| Amount (g) | 100 | See Ex. 5 | See Ex. 5 |
| Phenol (%) | 60 | See Ex. 5 | See Ex. 5 |
| $H_2O$ (%) | 1 | See Ex. 1 | See Ex. 1 |
| Others (%) | 39 | See Ex. 5 | See Ex. 5 |
| EXTRACTING SOLUTION | | | |
| Amount (g) | 500 | See Ex. 5 | See Ex. 5 |
| Sodium phenate (%) | 5 | See Ex. 5 | See Ex. 5 |
| RESULTS | | | |
| ORGANIC PHASE: | | | |
| Amount (g) | 41.4 | 36.2 | 39.5 |
| Phenol (%) | 26.4 | 17.2 | 24.6 |
| $H_2O$ (%) | 2.6 | 1.5 | 2.0 |
| Others (%) | 71.0 | 81.3 | 73.4 |
| INORGANIC PHASE: | | | |
| Amount (g) | 558.6 | 563.8 | 560.5 |
| Sodium phenate (%) | 4.5 | 4.4 | 4.5 |
| Free phenol (%) | 8.8 | 9.5 | 9.0 |
| EXTRACTION YIELD (%) | 81.9 | 89.3 | 83.8 |

TABLE 3

| | (% by weight) | |
|---|---|---|
| EXAMPLE | 8 | 9 |
| DATA | | |
| Temperature (°C.) | 50 | 50 |
| RECTIFICATION PURGE | | |
| Amount (g) | 5 | See Ex. 8 |
| Phenol (%) | 60 | See Ex. 8 |
| $H_2O$ (%) | 1 | See Ex. 8 |
| Others (%) | 39 | See Ex. 8 |
| EXTRACTING SOLUTION | | |
| Amount (g) | 50 | See Ex. 8 |
| Sodium phenate (%) | 5 | See Ex. 8 |
| RESULTS | | |
| ORGANIC PHASE: | | |
| Amount (l/h) | 2.4 | 2.2 |
| Phenol (%) | 5.1 | 0.20 |
| $H_2O$ (%) | 1.0 | 1.0 |
| Others (%) | 93.9 | 98.8 |
| INORGANIC PHASE: | | |
| Amount (l/h) | 52.6 | 52.7 |
| Sodium phenate (%) | 4.75 | 4.7 |
| Free phenol (%) | 5.40 | 5.6 |
| EXTRACTION YIELD (%) | 96.4 | 99.9 |

TABLE 4

| | (% by weight) | | |
|---|---|---|---|
| EXAMPLE | 10 | 11 | 12 |
| DATA | | | |
| Temperature (°C.) | 50 | See Ex. 10 | See Ex. 10 |
| RECTIFICATION PURGE | | | |
| Amount (g) | 100 | See Ex. 10 | See Ex. 10 |
| Phenol (%) | 60 | See Ex. 10 | See Ex. 10 |
| $H_2O$ (%) | 10 | See Ex. 10 | See Ex. 10 |
| Others (%) | 30 | 10 | 5 |
| EXTRACTING SOLUTION | | | |
| Amount (g) | 500 | See Ex. 10 | See Ex. 10 |
| Sodium phenate (%) | 15 | See Ex. 10 | See Ex. 10 |
| RESULTS | | | |
| ORGANIC PHASE: | | | |
| Amount (g) | 35.3 | 34.6 | 37.0 |
| Phenol (%) | 14.9 | 16.8 | 18.8 |
| $H_2O$ (%) | 1.5 | 1.5 | 2.0 |
| Others (%) | 83.6 | 81.7 | 79.2 |
| INORGANIC PHASE: | | | |
| Amount (g) | 564.7 | 565.4 | 563.0 |
| Sodium phenate (%) | 13.3 | 8.8 | 4.4 |
| Free phenol (%) | 9.7 | 9.6 | 9.4 |
| EXTRACTION YIELD (%) | 91.3 | 90.5 | 88.2 |

TABLE 5

| | (% by weight) | | |
|---|---|---|---|
| EXAMPLE | 13 | 14 | 15 |
| DATA | | | |
| Temperature (°C.) | 79 | 90 | 50 |
| RECTIFICATION PURGE | | | |
| Amount (g) | 100 | See Ex. 13 | See Ex. 13 |
| Phenol (%) | 60 | See Ex. 13 | See Ex. 13 |
| $H_2O$ (%) | 10 | See Ex. 13 | See Ex. 13 |
| Others (%) | 30 | See Ex. 13 | See Ex. 13 |
| EXTRACTING SOLUTION | | | |
| Amount (g) | 500 | See Ex. 13 | See Ex. 13 |
| Sodium phenate (%) | 5 | See Ex. 13 | See Ex. 13 |
| RESULTS | | | |
| ORGANIC PHASE: | | | |
| Amount (g) | 33.2 | 31.6 | 31.0 |
| Phenol (%) | 9.5 | 5.1 | 2.6 |
| $H_2O$ (%) | 1.0 | 0.5 | 0.6 |
| Others (%) | 89.5 | 94.4 | 96.8 |
| INORGANIC PHASE: | | | |
| Amount (g) | 556.8 | 568.4 | 569.0 |
| Sodium phenate (%) | 4.4 | 4.4 | 4.4 |
| Free phenol (%) | 10.0 | 10.3 | 10.4 |
| EXTRACTION YIELD (%) | 92.8 | 97.6 | 98.7 |

TABLE 6

| | (% by weight) | |
|---|---|---|
| EXAMPLE | 16 | 17 |
| DATA | | |
| Temperature (°C.) | 90 | 50 |
| RECTIFICATION PURGE | | |
| Amount (g) | 5 | See Ex. 16 |
| Phenol (%) | 60 | See Ex. 16 |
| $H_2O$ (%) | 10 | See Ex. 16 |
| Others (%) | 30 | See Ex. 16 |
| EXTRACTING SOLUTION | | |
| Amount (g) | 25 | See Ex. 16 |
| Sodium phenate (%) | 5 | See Ex. 16 |
| RESULTS | | |
| ORGANIC PHASE: | | |
| Amount (l/h) | 1.7 | 1.7 |
| Phenol (%) | 0.32 | 0.05 |
| $H_2O$ (%) | 1.0 | 1.0 |
| Others (%) | 98.7 | 99.0 |
| INORGANIC PHASE: | | |
| Amount (l/h) | 28.2 | 28.2 |
| Sodium phenate (%) | 4.4 | 4.4 |
| Free phenol (%) | 10.4 | 10.4 |
| EXTRACTION YIELD (%) | 99.8 | 99.97 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. In a process for recovering phenol from a rectification purge, containing from 20 to 90% by weight of phenol, in addition to various organic foreign matters, the improvement comprising subjecting said purge to an extraction operation, using, as an extracting solvent, an aqueous solution of an alkali metal phenate.

2. The process according to claim 1, wherein said phenate is sodium phenate.

3. The process according to claim 2, wherein said aqueous solution contains from 1 to 15% by weight of sodium phenate.

4. The process according to claim 2, wherein said aqueous solution contains from 5 to 15% by weight of sodium phenate.

5. The process according to claim 2, wherein said solution contains, in addition to sodium phenate, also free caustic soda (NaOH), the free soda amount being preferably lower than the amount necessary for the salification of all the phenol.

6. The process according to claim 5, wherein said free caustic soda (NaOH) is present in an amount of less than 50% of the amount necessary for salification of all the phenol.

7. The process according to claim 2, wherein the extraction temperature ranges from about room temperature to about 90° C.

8. The process according to claim 2, wherein the extraction temperature ranges from about 40° to about 80° C.

9. The process according to claim 2, wherein the extracting solvent amount ranges from 1 to 15 parts by weight per each part of purge.

10. The process according to claim 2, wherein the extracting solvent amount ranges from 5 to 15 parts by weight per each part of purge.

11. The process according to claim 1, wherein the extraction is carried out continuously, the aqueous solution being fed, in countercurrent, to an apparatus consisting of at least two mixers and at least two decanters.

12. The process according to claim 1, wherein the extraction is carried out continuously, the aqueous solution being fed, in countercurrent, to an apparatus permitting a plurality of extraction steps without requiring a physical separation of the purge from the extracting solvent.

13. The process according to claim 12, wherein the purge is an organic phase and is present as a continuous phase, while the aqueous phase is present as the dispersed phase.

14. The process according to claim 12, wherein the extraction is carried out in a tubular apparatus loaded with packing material.

15. The process according to claim 14, wherein said packing material is a material which is wetted by the organic phase.

16. The process according to claim 15, wherein said packing material is stainless steel.

17. A process for recovering phenol from a rectification purge containing from 20 to 90% by weight of phenol in addition to volatile organic foreign matters comprising subjecting said purge to an extraction with an aqueous solution containing 5–15% by weight of sodium phenate, at a temperature of from about 40° to about 80° C., wherein the solution amount ranges from about 5 to about 15 parts by weight per each part per weight of purge;

the organic phase is a continuous phase, whereas the aqueous phase is a dispersed phase; and continuously carrying out the extraction in countercurrent flow in a tubular apparatus, which tubular apparatus is loaded with stainless steel packing bodies.

18. The process according to claim 17, wherein said bodies are Raschig rings or Pall rings.

* * * * *